Figure 1:
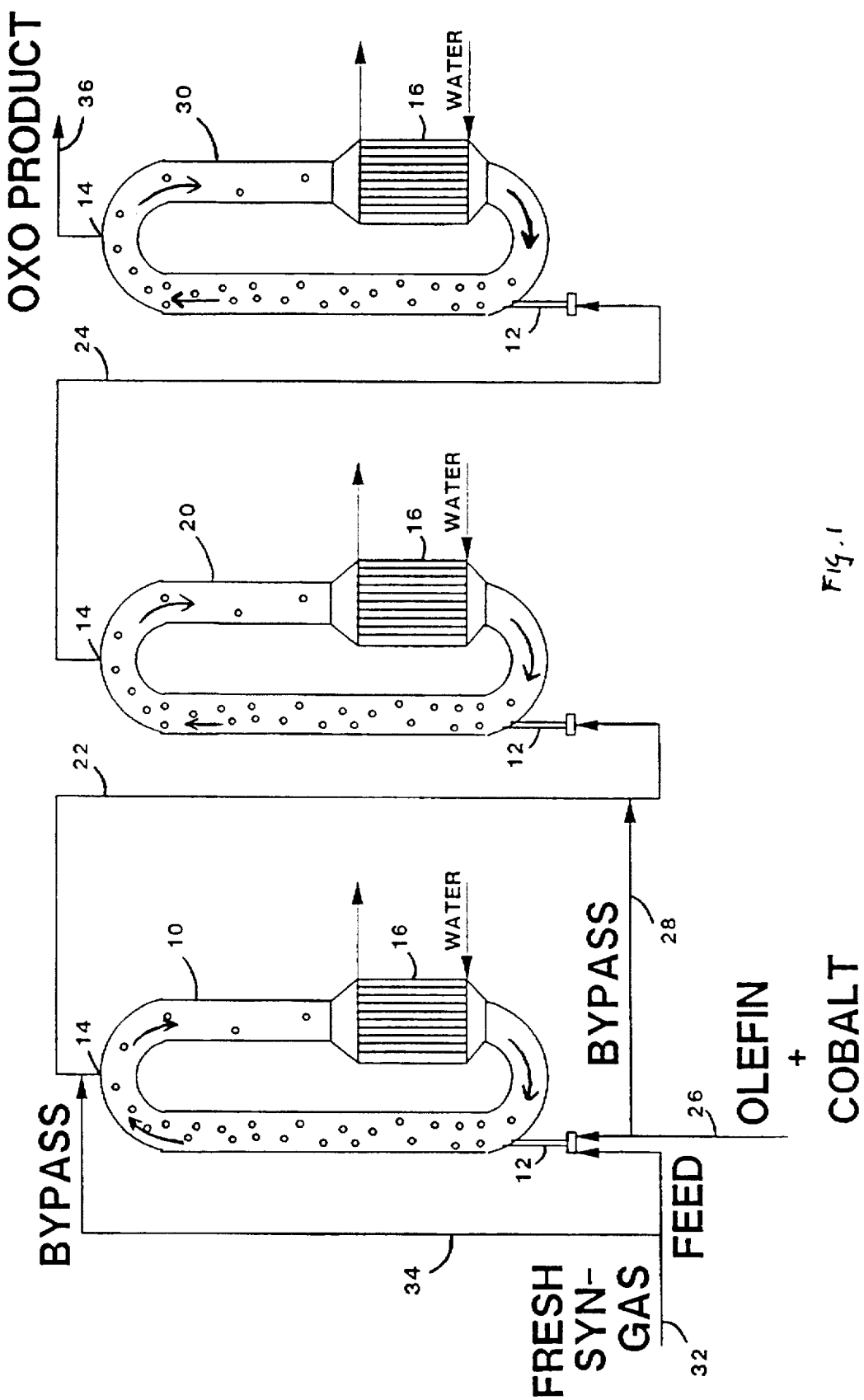

US005763678A

United States Patent [19]

Beckers et al.

[11] Patent Number: 5,763,678
[45] Date of Patent: Jun. 9, 1998

[54] HYDROFORMYLATION PROCESS EMPLOYING LOOP REACTORS

[75] Inventors: Hubertus Jozeph Beckers, Keerbergen, Belgium; Jan Martin De Rijke, Oostvoorne, Netherlands; Ronald Dean Garton, Baton Rouge, La.

[73] Assignee: Exxon Chemical Patents Inc, Houston, Tex.

[21] Appl. No.: 564,112

[22] PCT Filed: Jun. 14, 1994

[86] PCT No.: PCT/EP94/01936

§ 371 Date: May 1, 1996

§ 102(e) Date: May 1, 1996

[87] PCT Pub. No.: WO94/29018

PCT Pub. Date: Dec. 22, 1994

[30] Foreign Application Priority Data

Jun. 14, 1993 [GB] United Kingdom .................. 9312225

[51] Int. Cl.$^6$ ........................................................ C07C 45/50
[52] U.S. Cl. ................................................ 568/454; 568/451
[58] Field of Search ..................................... 568/451, 454

[56] References Cited

U.S. PATENT DOCUMENTS 4,312,837  1/1982  Papp et al. ............................ 422/224

FOREIGN PATENT DOCUMENTS 550233  3/1923  France .

*Primary Examiner*—Gary Geist
*Assistant Examiner*—Sreeni Padmanabhan
*Attorney, Agent, or Firm*—John F. Hunt

[57] ABSTRACT

An exothermic chemical reaction, for example, hydroformylation, is carried out in a series of loop reactors. Fresh reactant feed is supplied not only to the first reactor in the series but also to the second reactor, thereby achieving improved overall throughput while maintaining a stable temperature in at least the first reactor.

7 Claims, 1 Drawing Sheet

HYDROFORMYLATION PROCESS EMPLOYING LOOP REACTORS

This is the U.S. national stage application of PCT/EP 94/01936 filed Jun. 14, 1998 now WO 94/29018 published Dec. 22, 1994.

This invention relates to a chemical process, to apparatus for carrying out the process, and especially to a process carried out in a series of loop reactors, and more especially to hydroformylation carried out in such a series.

U.S. Pat. No. 4,239,930 (Allphin et al., assigned to Pearsall Chemical Company) describes the use of a series of liquid-filled pump-driven loop reactors for oligomerizing α-olefins in the presence of a promoted boron trifluoride catalyst. Fresh catalyst is pumped into each reactor in parallel, the entire olefin reactant feed being fed to the first reactor in the series.

U.S. Pat. No. 4,342,876 (Klingman, assigned to Bechtel International Corporation) describes the use of a loop reactor, in which circulation is gas-driven with excess gas being vented from the top of the reactor, in the oxidation of p-xylene and mentions the possibility of operating a number of such induced-flow reactors in series.

U.S. Pat. No. 4,312,837 (Papp et al., assigned to Produits Chimiques Ugine-Kuhlmann) describes an improved loop reactor for use in hydroformylation, the effect of the improvement being to retain some gas in the reaction mixture in the downward or return section of the loop. In the Example, the use of a series of three reactors is described.

It has been found, however, that at high throughputs temperature cycling of high amplitude takes place in the lead reactor in a series. These temperature instabilities could not be controlled by external cooling, and throughput reductions were necessary, resulting in a loss of efficiency.

The present invention provides a process for carrying out an exothermic chemical reaction in apparatus comprising a series of loop reactors, which comprises feeding reactants into the first reactor, transferring therefrom mixed reactants and reaction product to the second and any subsequent reactor in turn, and feeding a portion of at least one reactant directly to the second or a subsequent reactor.

More especially, the invention provides a process employing gaseous and liquid reactants, in which the material transferred from the first reactor is a mixture of reaction product and reactants, more particularly both gaseous and liquid reactants. In this case, it is advantageously a portion of a gaseous reactant that is fed directly to the second or subsequent reactor, optionally together with a portion of a liquid reactant.

More especially, the invention provides a process for hydroformylation of an olefin feedstock by syn gas in a series of loop reactors, which comprises feeding the olefin feedstock and syn gas to the first reactor, transferring therefrom mixed hydroformylation products and reactants to the second and any subsequent reactors in turn, and feeding a portion of syn gas directly to the second or a subsequent reactor.

Advantageously, a portion of both the syn gas and olefin feedstock is fed directly to the second or subsequent reactor.

It will be understood that by "directly" in the paragraphs above is meant that the reactant or feedstock is fed to the second or subsequent reactor without its having passed through a previous reactor.

The bypass of gaseous reactant enables the liquid reactant feed rate to be increased. However, at a certain feed rate, temperature oscillations recur, of a type known in the literature as "limit cycles". These are thermokinetic instabilities; at this point the capacity of the first reactor has been reached and liquid reactant is desirably also bypassed to the second or subsequent reactor.

The reader is referred to "Analysis of Limit Cycles in an Industrial Oxo Reactor", Vleeschhouwer, Carton, and Fortuin, Chem. Eng. Sci., 1992, 47, 2547, for a discussion of such temperature oscillations in loop reactors.

The present invention also provides apparatus comprising a series of loop reactors, each reactor being provided with reactant inlet means and product outlet means, the or each product outlet means of each reactor except the last being connected to the reactant inlet means of the next subsequent reactor, at least the second reactor being provided with means for supplying reactant in addition to that supplied by the product outlet means from the previous reactor.

More especially, the invention provides a hydroformylation reactor train comprising a series of loop reactors, the first reactor in the series being provided with olefin reactant feed means and syn gas feed means and product outlet means, each subsequent reactor being provided with reactant inlet means and product outlet means, the or each product outlet means of each reactor except the last being connected to the reactant inlet means of the next subsequent reactor, at least the second reactor being provided with means for supplying syn gas and optionally olefin reactant in addition to that supplied by the product outlet means from the previous reactor.

Advantageously, the second reactor is provided with means for supplying both additional syn gas and olefin reactant.

Typically each loop reactor will comprise at least two vertical tubes, means connecting the tops of the tubes and means connecting the bottoms, at least one of the vertical tubes being provided with cooling means. The tubes may be side by side or concentric.

Advantageously, in both the apparatus and the hydroformylation reactor train according to the invention circulation of reactants through each loop reactor is effected without the need for an external power supply, e.g., a pump, circulation being induced by the introduction of a reactant, especially a gaseous reactant.

As indicated above, it has been found that by providing an independent reactant feed to at least the second of the loop reactor series improved temperature stability results in the first reactor, allowing higher throughput in the reactor train.

Accordingly, the invention also provides, in apparatus comprising a series of loop reactors for carrying out exothermic reactions, the use of a bypass reactant feed line to at least the second loop reactor to improve reaction temperature stability in at least the first reactor.

More especially the invention also provides in a hydroformylation reactor train comprising a series of loop reactors, the first of which is provided with means for supplying the syn gas and means for supplying olefin reactant, the use of a syn gas bypass feed line to at least the second loop reactor to improve temperature stability at least in the first reactor. Advantageously, there is provided, for the same purpose, an olefin reactant bypass feed line to at least the second loop reactor.

The invention will be described below in more detail for simplicity with reference to a hydroformylation reaction but it will be understood that the principles of operation are more generally applicable.

The hydroformylation reaction, or oxo reaction, comprises the reaction of an olefinic species containing n carbon atoms with carbon monoxide and hydrogen (synthesis gas or syn gas) to yield an aldehyde and/or alcohol having n+1 carbon atoms. The reaction is normally carried out in the presence of a catalyst, usually a carbonyl, and more especially hydrocobalt carbonyl or dicobalt octacarbonyl.

The cobalt carbonyl is soluble or dispersible in the olefin, and is accordingly normally fed to a reactor together with the olefin, the conditions in the reactor being such as to maintain the olefin feed in the liquid phase.

The syn gas may be fed to the reactor through a separate inlet from that for the olefin feed, or the reactants may be mixed before being fed to the reactor. The temperature is maintained within a desired range by cooling, e.g., by using a water jacket. These general conditions apply to the first reactor in a series of loop reactors, when used in accordance with known techniques, subsequent reactors being fed with the mixture of reaction products and unreacted starting materials from the preceding reactor.

In accordance with the invention, a proportion of the syn gas feed is fed directly to the second loop reactor. This proportion may conveniently be up to 50%, advantageously from up to 30%, preferably the lowest proportion needed to maintain stable temperature conditions in the first reactor at the desired input rate.

If a proportion of the olefin feed also is fed directly to the second loop reactor, the proportion may conveniently be up to 50%, but again is preferably as low as needed to maintain first reactor stability.

The hydroformylation process of the invention may be carried out using any catalyst known in the art for catalysing hydroformylation reactions generally; conveniently, hydrocobalt carbonyl or dicobalt octacarbonyl is employed in catalytically effective proportions, e.g., from 0.05 to 3%, measured as metal, by weight, based on the weight of olefin feed, preferably in the range of from 0.05 to 1%, and more preferably from 0.25 to 0.5%.

In a four train oxo reactor train, it is within the scope of the invention to bypass the first reactor with two thirds of the total olefin and gas feed, one third of the feeds going to each of the second and third reactors; in this case, an increased catalyst concentration may be desirable.

The molar ratio of syn gas to olefin may conveniently be within the range of from 0.5:1 to 5:1, advantageously from 1:1 to 3:1 and preferably about 2:1. The volume ratio of hydrogen to carbon monoxide in the syn gas may be within the range of from 0.5:1 to 3:1, advantageously from 0.9:1 to 2:1, and preferably from 1:1 to 1.5:1.

The temperature of the reaction will depend on the identity of the olefin feed but is typically in the range of from 120° to 190° C. For a $C_9$ feed, a temperature in the range of from 165° to 190° C. may conveniently be employed, advantageously from 170° to 190° C. and preferably about 175° C. measured at the reactor outlet. A pressure of from 15 to 35 MPa may conveniently be employed, advantageously from 25 to 35 MPa, and preferably about 30 MPa.

Any olefin may be oxonated by the process of the invention, for example, from $C_2$ to $C_{20}$, advantageously $C_4$ to $C_{16}$, preferably $C_6$ to $C_{12}$, olefins, especially alkenes of such carbon numbers, which may be linear or branched.

One form of reactor train constructed in accordance with the invention will now be described in greater detail by way of example only with reference to the accompanying drawings, in which the sole FIGURE, is a flow diagram.

As shown in the FIGURE, a first loop reactor 10 is provided with a feed inlet 12 and a product outlet 14. The right-hand vertical section of the loop, the downleg, is provided with a heat exchanger 16 through which cooling water is passed. Second and third loop reactors 20 and 30 are similarly equipped. The outlet 14 from the first reactor 10 is connected by line 22 to the inlet 12 of the second reactor 20, and correspondingly the outlet 14 from the second reactor 20 is connected by line 24 to the inlet 12 of the third reactor. An olefin reactant line 26 is connected to the inlet 12 of the first reactor 10 and by a bypass line 28 to the line 22. (In practice, the olefin may be fed through more than one line to the first reactor, with the desired proportion of catalyst for the reaction being included in one or some only of the lines. The bypass may be taken from an olefin feed containing, or one not containing, the catalyst.) Similarly a syn gas line 32 is connected to the inlet 12 of the first reactor 10 and by a bypass line 34 to the line 22.

The outlet 14 of the third reactor 30 is connected to a product line 36.

In operation, olefin and catalyst are fed by line 26 and fresh syn gas by line 32 to the inlet 12 of the first loop reactor 10 and by lines 28, 34 and 22, to the inlet 12 of the second reactor 20. In the first reactor 10 the reactants are circulated in the direction of the arrows, the exotherm of the reaction being controlled by the flow of temperature controlled cooling water through the heat exchanger 16. A minor proportion of the reaction mixture is removed through the outlet 14 and transferred, together with fresh syn gas and olefin feedstock, by the line 22 to the second reactor 20. The major proportion of the reaction mixture continues to circulate in the first reactor. The internal circulation rate is advantageously from 10 to 25 times the liquid feed flow rate, enabling the loop reactor to function as a continuous stirred tank reactor with only very small temperature and concentration gradients.

In the second and third reactors 20 and 30, further reaction takes place, and product is taken off through the line 36.

The following examples illustrate the invention.

EXAMPLE 1

To a three reactor series as described above were fed an olefin feedstock, containing 99% by weight isononene and 1% isononane, mixed with 0.362 wt % cobalt (measured as metal, in the form of hydrocobalt carbonyl), and syn gas, $H_2$:CO 1.4:1 by volume, in a total molar proportion of olefin:syn gas of 1:2.58. The total olefin feed was passed to the first reactor, while 80% of the syn gas was passed to the first reactor and 20% to the second.

All the reactors were maintained at a temperature of about 172° C. measured at the reactor outlet.

Analysis of the degassed oxo product taken from the outlet from the third reactor showed that it contained 7.7% by weight of unreacted nonenes, indicating a conversion rate of 90.6%.

Observation of the first reactor outlet temperature showed a substantially constant temperature of about 172° C. on which was superimposed a small periodic oscillation, of amplitude about 1° C. and period about 1 minute.

To effect a comparison, the bypass line 34 was closed, the total volume of syn gas now passing through the first reactor, the remaining operating conditions being retained. The first reactor outlet temperature now varied between 165° C. and 185° C. in the course of 20 minutes, with superimposed oscillations of amplitude up to 15° C. and period about 90 seconds. After 1 hour of unstable operation, the bypass line 34 was reopened to enable 20% of the syn gas to be fed to the second reactor, and as a consequence the first reactor returned to its previous steady state operation.

Without syn gas bypass, stable operation was achievable only at a throughput at most approximately 85% of that available with syn gas bypass.

EXAMPLE 2

To a three reactor series as described above were fed an olefin feedstock, containing 99% by weight isononene and 1% isononane, mixed with 0.362 wt % cobalt (measured as metal, in the form of hydrocobalt carbonyl), and syn gas, $H_2:CO$ 1.4:1 by volume, in a total molar proportion of olefin:syn gas of 1:2.95. 80% of the olefin feed was passed to the first reactor and 20% to the second reactor, while 75% of the syn gas was passed to the first reactor and 25% to the second.

All the reactors were maintained at a temperature of about 175° C. measured at the reactor outlet.

The degassed oxo product taken from the outlet from the third reactor was analysed and found to contain 9.2% by weight unreacted nonenes, indicating an 88.7% conversion factor.

Observation of the first reactor outlet temperature showed a substantially constant temperature of about 175° C. on which was superimposed a small periodic oscillation, of amplitude about 3° C. and period about 1 minute. When the reactor train was operated at the same throughput with all the olefin feedstock passing through the first reactor, the first reactor outlet temperature varied between 140° C. and 180° C. in a limit cycle with a period of about 25 minutes, with superimposed oscillations of amplitude up to 5° C. and a period of about 80 seconds.

By incorporating reactant feed bypass, the maximum throughput through the reactor series consistent with temperature stability was increased by about 40%, compared to the maximum throughput available with neither syn gas nor olefin feed bypass. Taking into account the slight reduction in conversion factor, the mass of olefin converted was increased by about 35%.

We claim:

1. A process for catalytic hydroformylation of an olefin feedstock by syn gas in a series of loop reactors, comprising feeding the olefin feedstock, syn gas, and catalyst to the first reactor, transferring therefrom mixed hydroformylation products and reactants to the second and any subsequent reactors in turn, and feeding a portion of syn gas to the second or a subsequent reactor without its having passed through a previous reactor.

2. The process of claim 1 wherein syn gas and olefin feedstock are both fed directly to the second or subsequent reactor.

3. The process of claim 1 wherein circulation of reactants through each loop reactor is effected by the introduction of a gaseous reactant.

4. The process of claim 1 wherein there is a series of at least three reactors.

5. The process of claim 1 wherein a reactant is syn gas, and wherein up to 50% syn gas is fed directly to the second or subsequent reactor.

6. The process of claim 1 wherein a reactant is an olefin, and wherein up to 50% of the olefin is fed directly to the second or subsequent reactor.

7. The process of claim 6 wherein said olefin is a $C_4$ to $C_{16}$ alkene.

* * * * *